United States Patent
Wu et al.

(10) Patent No.: US 7,291,308 B2
(45) Date of Patent: Nov. 6, 2007

(54) ENDOSCOPE IMMERSION TRAY

(75) Inventors: Su-Syin S. Wu, Irvine, CA (US); Josh Hagerman, Corona Del Mar, CA (US); Michael J. Simmons, Milford, MI (US); Idemudia Ehigiato, Belleville, MI (US); Scott D. Godfrey, Dearborn, MI (US)

(73) Assignee: Ethicon, Inc., Somerville, NJ (US)

( * ) Notice: Subject to any disclaimer, the term of this patent is extended or adjusted under 35 U.S.C. 154(b) by 4 days.

(21) Appl. No.: 10/928,959

(22) Filed: Aug. 27, 2004

(65) Prior Publication Data

US 2006/0045798 A1    Mar. 2, 2006

(51) Int. Cl.
*A61L 2/16* (2006.01)

(52) U.S. Cl. ................ 422/28; 422/40; 422/292; 422/300

(58) Field of Classification Search ........... 422/292, 422/300, 28, 40
See application file for complete search history.

(56) References Cited

U.S. PATENT DOCUMENTS

| | | | |
|---|---|---|---|
| 4,053,280 A | 10/1977 | Salisbury | |
| 4,620,527 A * | 11/1986 | Adams, Jr. | 600/102 |
| 5,090,433 A | 2/1992 | Kamaga | |
| 5,711,921 A | 1/1998 | Langford | |
| 5,906,802 A | 5/1999 | Langford | |
| 5,954,637 A * | 9/1999 | Francis | 600/138 |
| 6,132,691 A * | 10/2000 | Coles | 422/300 |
| 6,528,015 B1 | 3/2003 | Lin et al. | |
| 6,932,099 B2 * | 8/2005 | Mahaney | 137/15.08 |

FOREIGN PATENT DOCUMENTS

| | | |
|---|---|---|
| DE | 0303115 A2 * | 2/1989 |
| DE | 29914133 U1 | 1/2000 |
| FR | 2501045 A | 9/1982 |
| GB | 2094150 A | 9/1982 |
| GB | 2251382 A | 7/1992 |
| JP | 2000-225126 A | 8/2000 |
| JP | 2002/25126 A | 1/2002 |
| JP | 2002-238847 A | 8/2002 |
| RU | 2030920 C1 * | 3/1995 |

OTHER PUBLICATIONS

European Search Report re: EP 05 25 5257 dated Oct. 28, 2005.
OE-C11, Soaking Cap for PENTAX Ultrasound G.I Endoscopes.

* cited by examiner

*Primary Examiner*—Gladys J P Corcoran
*Assistant Examiner*—Sean E Conley

(57) ABSTRACT

A system provides for high level disinfection or sterilization of an endoscope having a first portion adapted for immersion and a second portion not adapted for immersion. The system includes a container having a first basin sized and adapted to receive the first portion of the endoscope for immersion, a separate and adjacent second basin sized and adapted to receive the second portion of the endoscope, a wall between the first basing and the second basin, and a trough in an upper portion of the wall between the first basin and second basin through which a tube connecting the first portion of the endoscope and the second portion of the endoscope may extend.

7 Claims, 4 Drawing Sheets

ENDOSCOPE IMMERSION TRAY

BACKGROUND OF THE INVENTION

The present invention relates to systems and methods for high level disinfection or sterilization of endoscopes through immersion into disinfecting or sterilization liquids and more particularly to the immersion of endoscopes having liquid sensitive portions.

After a thorough cleaning, high level disinfection or sterilization of an endoscope employing a liquid disinfectant or sterilant solution is frequently performed in a basin. The basin is filled with the solution and the solution is tested to ensure it is of sufficient concentration. The endoscope is immersed within the solution and all of the endoscope channels are filled with the solution. Typically, the basin is covered with a lid. The endoscope then soaks within the solution for a time period sufficient to achieve the desired level of disinfection or sterilization. After the immersion, the endoscope is processed to remove the sterilant and any rinsing liquids.

While many endoscopes are designed to be completely immersed, some endoscopes, such as those having ultrasonic scanners, have sensitive electronics which are not completely sealed from moisture. These electronics would be damaged through immersion and thus at least this portion of the endoscope is not suitable for immersion within the disinfecting or sterilization solution. Current immersion practice with such endoscopes involves leaving that sensitive portion outside of the basin and immersing the remainder of the endoscope. However, some of the disinfecting or sterilization solution may leak out along the flexible tubes of the endoscope to reach electronic portion and to reach surfaces upon which it has been placed. Since this solution by its very nature tends to be hazardous, such releases of solution from the basin are to be discouraged.

SUMMARY OF THE INVENTION

A method, according to the present invention, provides high level disinfection or sterilization of an endoscope having a first portion adapted for immersion and a second portion not adapted for immersion. The method includes the steps of: placing the first portion of the endoscope into a first basin of a container; placing the second portion of the endoscope into a separate second basin of the container; immersing the first portion of the endoscope in a disinfecting or sterilization solution in the first basin; and not immersing the second portion of the endoscope.

Preferably, the method further includes the step of covering at least the first basin, but more preferably both the first and second basins, with a lid.

Preferably, the first basin is sealed from the second basin, such as by interposing a conformable seal between the lid and the container, with the seal conforming around the endoscope where it passes between the first basin and the second basin.

Preferably, the method further includes the step of resting that portion of the endoscope within the second basin upon upwardly extending protrusions so as to elevate it above a lower surface of the second basin and thereby prevent immersion in any solution accidentally carried over into the second basin.

Preferably, a tube connecting the first portion of the endoscope and second portion of the endoscope is passed through a trough in a wall between the first basin and second basin.

Preferably, the method includes the step of draining any fluid from the second basin to the first basin to keep the second basin essentially free of fluid.

Suitable disinfection or sterilization solutions preferably include one or more active ingredients selected from the group of gluteraldehyde, ortho-phthalaldehyde, peracetic acid, hydrogen peroxide, performic acid, chlorine or hydrochloride generating solutions, and ozone containing or generating solutions, most preferably from gluteraldehyde and ortho-phthalaldehyde.

A system, according to the present invention, provides for high level disinfection or sterilization of an endoscope having a first portion adapted for immersion and a second portion not adapted for immersion. The system comprises a container having a first basin sized and adapted to receive the first portion of the endoscope for immersion, a separate and adjacent second basin sized and adapted to receive the second portion of the endoscope, a wall between the first basin and the second basin; and a trough in an upper portion of the wall between the first basin and second basin through which a tube connecting the first portion of the endoscope and the second portion of the endoscope may extend.

Preferably, the system includes instructions for use which thereof, said instructions including directions for immersing the first portion of the endoscope in a disinfecting or sterilization solution in the first basin and placing the second portion of the endoscope into the second basin and not immersing the second portion of the endoscope.

DETAILED DESCRIPTION

Figure 1:
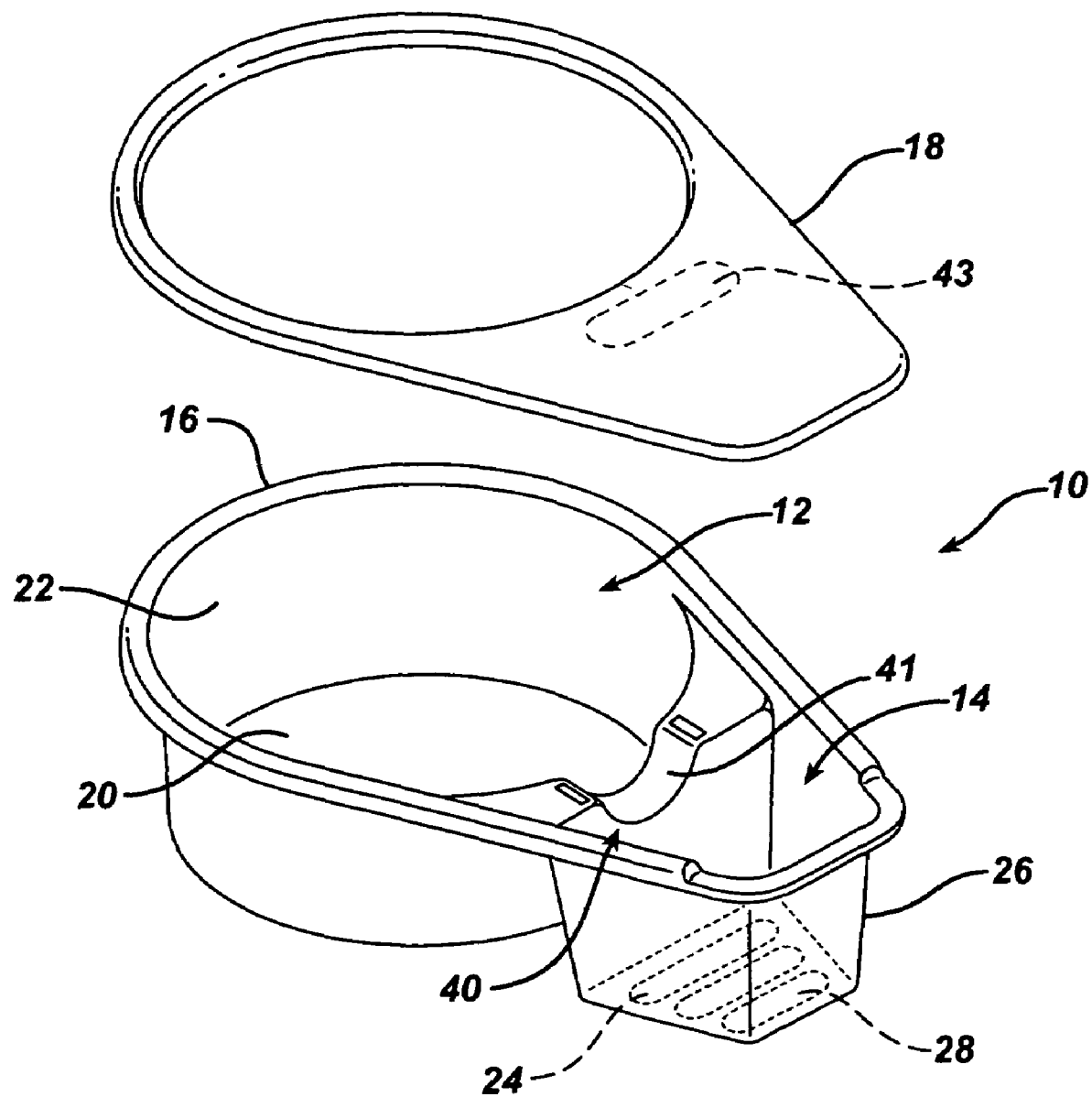
FIG. 1 is a perspective view of a container system according to the present invention for high level disinfection or sterilization of an endoscope having a non-immersible portion thereof.

FIG. 1 illustrates a container 10 according to the present invention. It comprises a large first basin 12 for receiving an endoscope (not shown in FIG. 1) for immersion and an adjacent smaller second basin 14 for receiving non-submersible portions of the endoscope. A lip 16 encircles an upper portion of the container 10 and provides a sealing surface against which a cover 18 may seal. The large basin comprises a circular bottom wall 20 and a side wall 22 extending upwardly therefrom. Of course other shapes are possible. The smaller basin 14 comprises a bottom wall 24 having the shape of a truncated pyramid and side walls 26 extending upwardly therefrom. A series of ribs 28 extend upwardly from the bottom wall 24 and serve to elevate that portion of the endoscope in the small basin 14 above the bottom wall 24 to prevent immersion thereof in any carryover liquid which may travel into the small basin 14.

Figure 2:
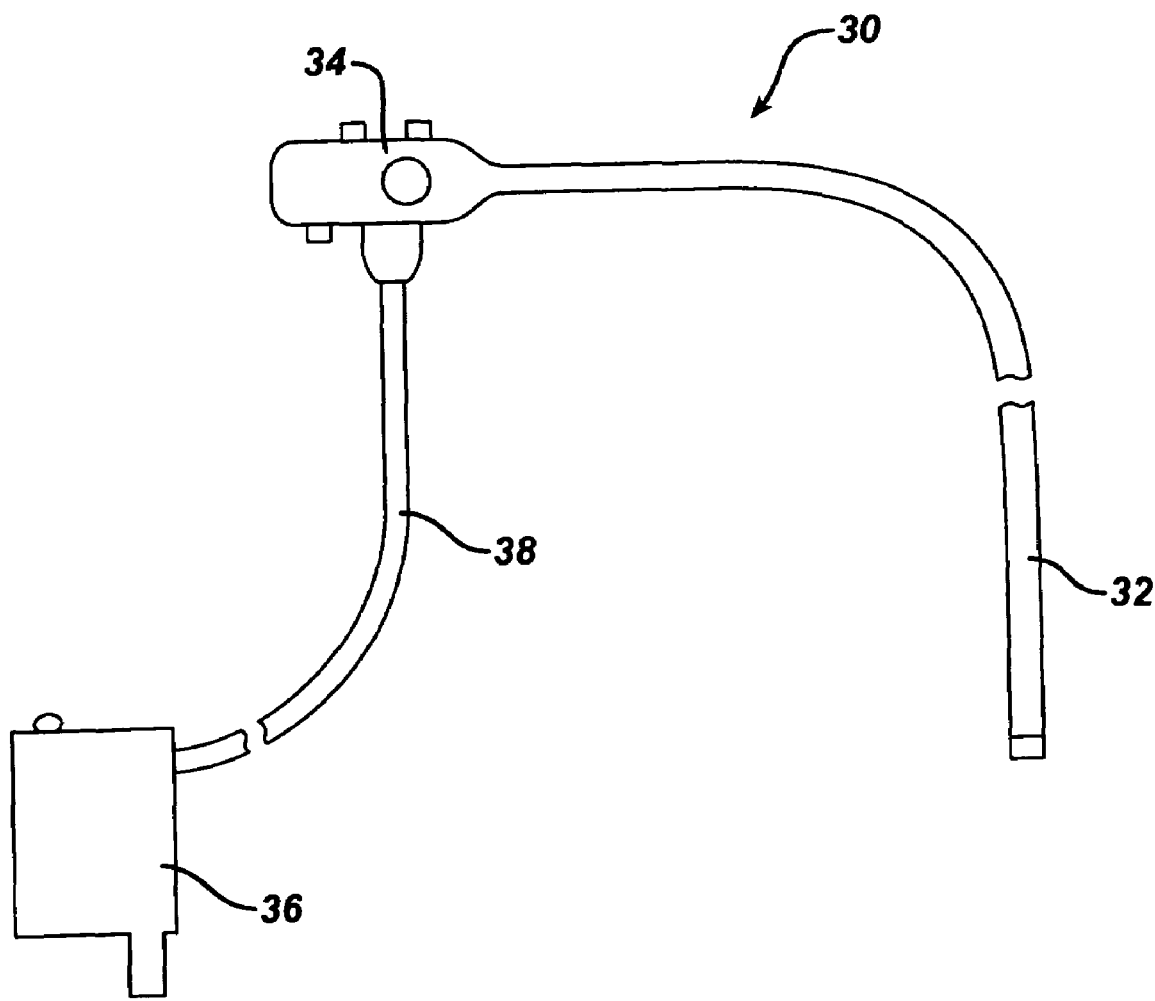
FIG. 2 is a perspective view of an endoscope for disinfection or sterilization within the container system of FIG. 1.

FIG. 2 illustrates an endoscope 30 of a type which might be processed in the container 10. It comprises a flexible insertion portion 32 connected to a control head 34. It also comprises a scanner unit 36 connected via a flexible tube 38 to the control head 34. It is the scanner 36 which generally is not susceptible to an immersion during the disinfection process. The endoscope 30 illustrated in FIG. 2 is but one example of an endoscope having a portion not susceptible to immersion. Many other designs carry this limitation.

Figure 3:
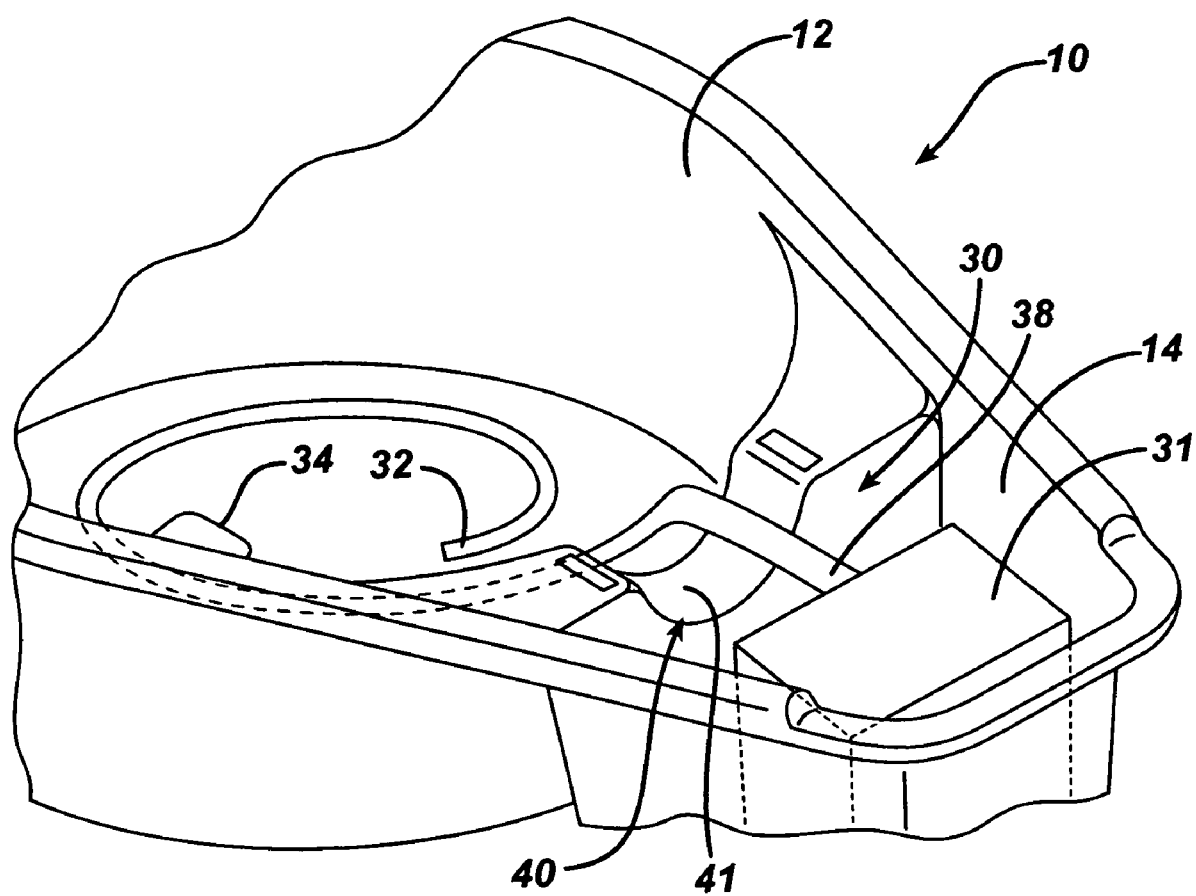
FIG. 3 is a detail view of a portion of the container system of FIG. 1.

FIG. 3 illustrates how the endoscope 30 sits within the container 10, with the scanner 36 in the smaller basin 14 and the insertion tube 32 and control head 34 in the large basin 12. The flexible tube 38 between the scanner 36 and control head 34 passes through a trough 40 between the side walls 22 of the large basin 12 and 26 of the small basin 14.

As shown in FIGS. 1 to 3, the arrangement of the container 10 with one basin 12 for the bulk of the endoscope 30 and a separate basin 14 for liquid sensitive portions of the endoscope 30 allows efficient high level disinfection or sterilization of those portions of the endoscope 30 susceptible to immersion while simultaneously protecting those portions of the endoscope 30 not susceptible to immersion and preventing carryover of disinfecting solution out of the container 10. The trough 40 substantially aids in preventing solution from transferring into the smaller basin 14 and the ribs 28 protect the scanner section 36 even if solution gets into the small basin 14. An elastomeric seal or seals 41 can be provided at the trough 40 to seal the trough 40 and flexible tube 38 to further limit fluid carryover from the large basin 12 to the small basin 14. Adding an additional seal 43 on the lid 18 in registry with the trough 40 enhances the sealing.

Figure 4:
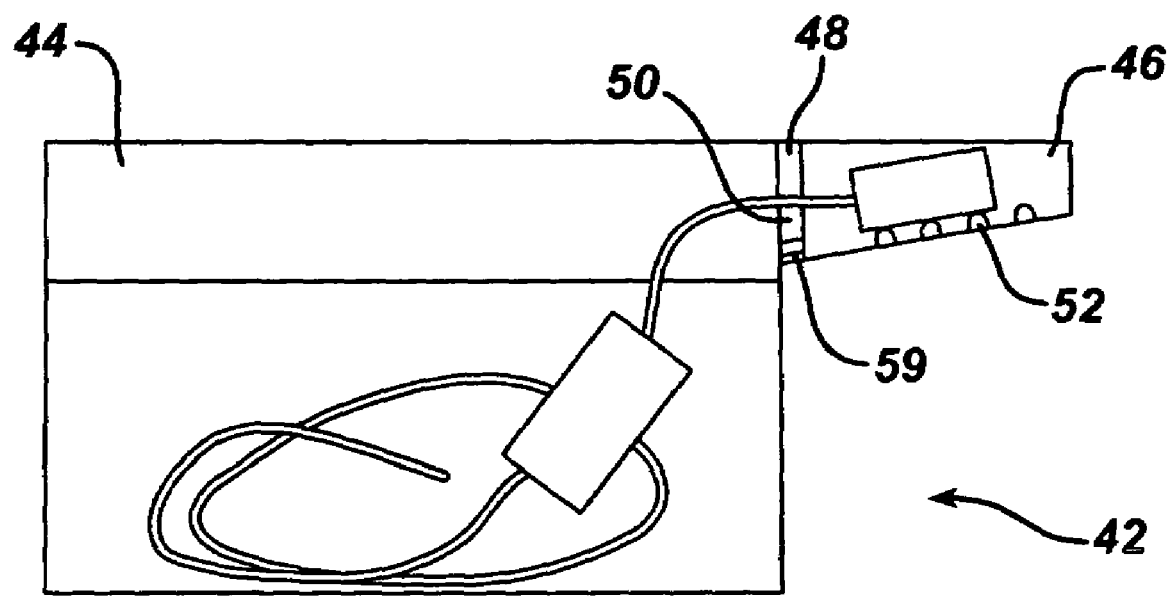
FIG. 4 is an alternative embodiment of a container system according to the present invention for high level disinfection or sterilization of an endoscope having a non-immersible portion thereof.

FIG. 4 illustrates an alternative embodiment of a container 42. In this embodiment, a large basin 44 holds the bulk of the endoscope and a small basin 46 connected thereto holds the scanner 36 a wall 48 separates the large and small basins 44 and 46 and has a trough 50 therethrough as in the previous embodiment. Upwardly extending protrusions 52 elevate the scanner 36 in the small basin 46. Departing from the prior embodiment, drainage, as through apertures 54 or deep troughs is allowed from the small basin 46 to the large basin 44. Thus, any fluid which makes its way into the small basin 46 will drain back into the large basin.

The container 10 is preferably formed of materials not susceptible to long or short term degradation by the desired disinfection/sterilization solution. Suitable materials include, without limitation, polyethylene (either high density or low density), polypropylene, polyvinyl chloride (PVC), acrylonitrile-butadiene-styrene (ABS), polycarbonate (PC), polyether imide (PEI), polysulfone (PS), polyether sulfone (PES), polyphenyl sulfone (PPS), liquid crystal polymers (LCP), and polytetrafluoroethylene (PTFE). Some materials can be more desirable when designing the container 10 to be compatible with multiple disinfection and sterilization solutions, particularly polypropylene, PEI, PS, PC and PPS.

The material chosen to some degree determines the preferred forming techniques as will be understood by those of skill in the art. Preferred construction methods include injection molding, thermoforming and transfer molding. Other primary polymer processing methods, such as roto-molding and casting, may be employed. Secondary polymer processing methods, such as machining, drilling, cutting, melt bonding and gluing, can be use to complete the construction and connect various portions of the tray or to attach the seal or seals 41.

The following description of operation refers to FIGS. 1 to 3. However, operation with the embodiment of FIG. 4 is similar. After a medical procedure the endoscope 30 is thoroughly cleaned according to the manufacturers instructions and prepared for immersion in the container 10. Typically the cleaning will involve block and leak testing of the endoscope channels, a manual cleaning, as with an enzymatic detergent, of the exterior as well as a manual cleaning of any endoscope channels suitable to receive a cleaning brush. Remaining channels are flushed with cleaning detergent and the entire endoscope and channels are then rinsed.

The endoscope 30 is then immersed in a suitable disinfecting or sterilization solution such as gluteraldehyde (available from Advanced Sterilization Products Division Ethicon Inc., Irvine, Calif. under the trademark CIDEX®) or ortho-phthalaldehyde (available from Advanced Sterilization Products Division Ethicon Inc., Irvine, Calif. under the trademark CIDEX®-OPA). Other possible disinfection or sterilization liquids includes without limitation, peracetic acid, hydrogen peroxide, performic acid, chlorine or hydrochloride generating chemical solutions, such as hypochlorite, hypochlorous acid and chlorine dioxide, and ozone containing or generating chemical solutions. Combinations of any of these liquids can be used, either together or sequentially.

Typically the solution is tested with a test strip to ensure that it is of the required potency. Then all of the endoscope 30 with the exception of the scanner section 36 is placed into the large basin 12 in such a fashion as to maximize filling of the lumens of the endoscope. The scanner portion 36 is placed into the smaller basin 14 with the flexible tube 38 extending through the trough 40. Additional solution is manually squirted into the endoscope lumens (not shown) as for example via a syringe. The scanner portion 36 is typically treated by wiping it with the solution which does not effect the same level of disinfection as immersion, yet suffices as this part of the endoscope 30 is not inserted into a patient and in fact should not contact the patient.

The lid 18 is placed onto the container 10 and the endoscope 30 remains immersed for a sufficient period of time to effect the desired level of cleaning or disinfection. After that time has passed the endoscope is removed from the container 10 and rinsed with sterile water, the channels flushed with alcohol and purged with air to ensure that they are dry. The endoscope 30 is now ready for its next use.

While the invention has been particularly described in connection with specific embodiments thereof, it is to be understood that this is by way of illustration and not of limitation, and that the scope of the appended claims should be construed as broadly as the prior art will permit.

What is claimed is:

1. A method of providing high level disinfection or sterilization of an endoscope having a first portion adapted for immersion and a second portion not adapted for immersion, the method comprising the steps of:
    placing the first portion of the endoscope into a first basin of a container;
    placing the second portion of the endoscope into a separate second basin of the container;
    immersing the first portion of the endoscope in a disinfecting or sterilization solution in the first basin;
    not immersing the second portion of the endoscope;
    covering the first basin and the second basin with a lid; and
    sealing the first basin from the second basin.

2. A method according to claim 1 and further comprising sealing the first basin from the second basin by interposing a conformable seal between the lid and the container, the seal conforming around the endoscope where it passes between the first basin and the second basin.

3. A method according to claim 1 and further comprising the step of resting that portion of the endoscope within the second basin upon upwardly extending protrusions so as to elevate it above a lower surface of the second basin whereby to prevent immersion in any solution accidentally carried over into the second basin.

4. A method according to claim 1 wherein the disinfection or sterilization solution comprises one or more active ingredients selected from the group of gluteraldehyde, orthophthalaldehyde, peracetic acid, hydrogen peroxide, performic acid, chlorine or hydrochloride generating solutions, and ozone containing or generating solutions.

5. A method according to claim 1 wherein the disinfection or sterilization solution comprises gluteraldehyde or orthophthalaldehyde.

6. A method of providing high level disinfection or sterilization of an endoscope having a first portion adapted for immersion and a second portion not adapted for immersion, the method comprising the steps of:

placing the first portion of the endoscope into a first basin of a container;

placing the second portion of the endoscope into a separate second basin of the container;

immersing the first portion of the endoscope in a disinfecting or sterilization solution in the first basin;

not immersing the second portion of the endoscope;

passing a tube connecting the first portion of the endoscope and second portion of the endoscope through a trough in a wall between the first basin and second basin; and covering the first basin and the second basin with a lid.

7. A method of providing high level disinfection or sterilization of an endoscope having a first portion adapted for immersion and a second portion not adapted for immersion, the method comprising the steps of:

placing the first portion of the endoscope into a first basin of a container;

placing the second portion of the endoscope into a separate second basin of the container;

immersing the first portion of the endoscope in a disinfecting or sterilization solution in the first basin;

not immersing the second portion of the endoscope; and draining any fluid from the second basin to the first basin to keep the second basin essentially free of fluid.

* * * * *